United States Patent [19]

Baker et al.

[11] Patent Number: 4,870,168

[45] Date of Patent: Sep. 26, 1989

[54] 3-UNSATURATED ALKYL CEPHEMS FROM 3-TRIFLYL CEPHEMS

[75] Inventors: Stephen R. Baker, Cicero; Vittorio Farina, Syracuse; Chester Sapino, Jr., East Syracuse, all of N.Y.

[73] Assignee: Bristol-Myers Company, New York, N.Y.

[21] Appl. No.: 19,396

[22] Filed: Feb. 26, 1987

[51] Int. Cl.[4] ............................................ C07D 501/20
[52] U.S. Cl. .................................... 540/222; 540/219; 540/225; 556/86
[58] Field of Search ....................... 540/219, 222, 225; 556/86

[56] References Cited

U.S. PATENT DOCUMENTS 3,959,324  5/1976  Peterson ................................ 556/86

OTHER PUBLICATIONS

Scott (I) (1984) J. Am. Chem. Soc., v. 106, p. 4630-4632.
Scott (II) (1986) J. Am. Chem. Soc., v. 108, pp. 3033-3040.

*Primary Examiner*—Donald G. Daus
*Attorney, Agent, or Firm*—Robert E. Carnahan

[57] ABSTRACT

There is disclosed a process for the production of certain 3-hydrocarbyl-3-cephem derivatives wherein the hydrocarbyl group is selected from 1-alkenyl and conjugated and unconjugated 1-polyalkenyl, 1-alkynl, carbocyclic and heterocyclic aryl, and carbocyclic and heterocyclic arylmethyl and, in the case of the 1-alkenyl and conjugated 1-polyalkenyl derivatives, with substantially complete stereospecificity, by coupling a 3-triflyloxy cephem with a hydrocarbyltributylstannane in the presence of bis(dibenzylideneacetonyl)-palladium, a phosphine, and a metal halide such as, for example, zinc chloride. The 3-unsaturated alkyl-3-cephem derivatives so-produced are useful as broad-spectrum antibacterial agents.

7 Claims, No Drawings

3-UNSATURATED ALKYL CEPHEMS FROM 3-TRIFLYL CEPHEMS

BACKGROUND OF THE INVENTION

1. Field of the Invention

The present invention relates to a process for the production of a 3-hydrocarbyl-3-cephem derivative by providing a 3-triflyloxy-3-cephem intermediate, reacting the intermediate with a 1-alkenyltributylstannane in the presence of bis(dibenzylideneacetonyl)-palladium and a phosphine and a metal halide. The resulting 3-unsaturated alkyl-3-cephems are useful as broad spectrum antibacterial agents.

2. Background Art

Hoshi et al., U.S. Pat. Nos. 4,591,641 (5/86) and 4,520,022 (5/85), both of which are owned by the assignee of the present invention, disclose vinyl-substituted cephalosporins having the 3-((Z)-1-propenyl) and 7-phenylglycylamido groups represented by the structural formula, A,

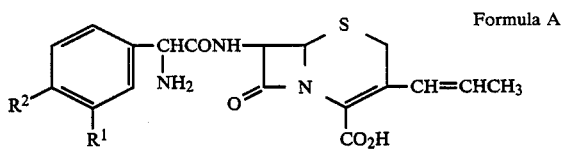

Formula A wherein the 3-propenyl group has the (Z) configuration. These patented compounds were produced by forming a substituted vinyl group in the 3-position of the cephalosporin nucleus by reacting a 3-halomethyl cephalosporin or an alkyl halide (e.g., methyl halide) with a triarylphosphine to yield a phophoranyl intermediate which is then treated with a alkylhydrogencarbonyl reagent or a 3-hydrogencarbonyl cephalosporin, respectively. The foregoing compounds were produced by application of the synthetic routes disclosed in U.S. Pat. Nos. 3,769,277 (10/73), 3,994,884 (11/76), and 4,107,431 (8/78).

Long et al., U.S. Pat. No. 3,769,277 (10/73)disclose $\Delta^3$-4-carboxy cephalosporins of the formula

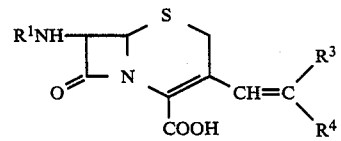

by reacting a 3-formyl (i.e. a 3-hydrogencarbonyl)cephalosporin with a phosphorane of the formula R3P=CR3R4

Weir, U.S. Pat. No. 3,994,884 (11/76) discloses the preparation of -66 $^3$-4-carboxy cephalosporin having a 3-vinyl group by reacting the corresponding 3-halomethyl cephalosporin compound with a phosphine to obtain the phosphonium intermediate, converting the phosphonium intermediate to the corresponding phosphoranylidene intermediate, and coupling the phosphoranylidene intermediate with formaldehyde.

Clark, et al., U.S. Pat. No. 4,107,431 (8/78) (GB No. 1342241), disclose the preparation of $\Delta^3$-vinyl or substituted vinyl-4-carboxy cephalosporins by reacting a 3-phosphoranylidene cephalosporin with a carbonyl compound of the formula R3COR4 or by reacting a 3-formyl cephalosporin with a phosphorane of the formula O'Callaghan et al., U.S. Pat. No. 3,830,700 (8/74), disclose certain 3-arylvinvyl cephalosporins useful as chromogenic agents for the detection of β-lactamase activity. The compounds useful in the patented method were prepared by reacting a 3-phosphoranylidene cephalosporin with a hydrogencarbonyl aryl (aryl aldehyde) compound or by reacting a 3-hydrogencarbonyl cephalosporin with a phosporane of the formula (R)3P=CHAr.

Beeby, U.S. Pat. Nos. 3,983,113 (9/76), 4,049,806 (9/77), and 4,139,618 (2/79) disclose 3-(heterocyclothio)propenyl cephalosporins represented by the formula

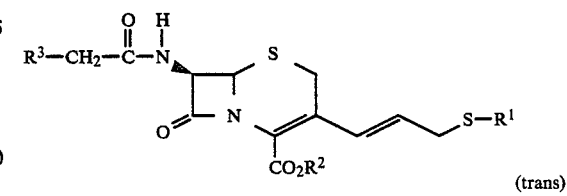

(trans)

wherein the compounds were prepared by reacting the starting 3-formyl cephalosporin with a suitable vinyl Grignard reagent to obtain a mixture of α- and β-hydroxy isomers of the corresponding 3-(1-hydroxyprop-2-enyl) cephalosporin followed by treating the foregoing intermediate with a mercapto substituted heterocycle corresponding to the SR1 substituent in the presence of a small amount of strong acid. Beeby, U.S. Pat. No. 4,112,087 (9/78) discloses compound having the formula shown above except that "OR" is substituted for "S-R1"

Webber, U.S. Pat. No. 4,065,620 (12/77) discloses 3-(substituted) vinyl cephalosporins prepared by reacting a 3-formyl cephalosporin compound with a phosphorane of the formula R1R2R3P=CH-Y under conventional Wittig reaction conditions.

Takaya et al., EP App. Publn. 0,030,630 (6/81) disclose 7-acylamino-3-vinylcephalosporanic acid derivatives prepared by reacting a 3-formyl cephalosporin compound with a suitable phosphorane.

Miyadera et al., U.S. Pat. No. 4,147,863 (4/79) disclose cephalosporin derivatives having a (1-alkyl-1H-tetrazol5-yl)vinyl group at the 3-position of the cephem nucleus. The patent discloses preparation of the intermediate having the given 3-vinyl substituent by reacting a known 3-formyl cephalosporin with a Wittig reagent (phosphorane).

Beattie et al., U.S. Pat. No. 4,255,423 (3/81) disclose cephalosporin compounds having a substituted or unsubstituted vinyl group at the 3-position of the cephalosporin nucleus prepared by the reaction of a phosphoranylidene compound with a compound containing a carbonyl group. More particularly, a phosphoranylidene compound of the formula

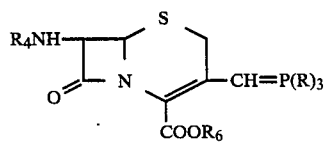

may be reacted with a carbonyl compound of the formula R2-CO-R3 to obtain the -CH=CR2R3 substituent at the 3-position of the cephem nucelus.

It is known in the art to which this invention and the compounds thereby produced relate that the compounds having the cis(Z)-stereoisomeric configuration are preferred over the compounds having the trans(E)-stereoisomeric configuration because the former compounds possess greater antibacterial activity,. (See U.S. Pat. No. 4,520,022, col. 16, lines 23-29).

The processes heretofore known and reported in the literature for producing 3-(1-propenyl)-3-cephems afford a mixture of the cis(Z)- and trans(E)-isomers which requires costly separation to obtain the preferred, more antibacterially active cis(Z)-isomer and, accordingly, the overall yield of desired cis(Z)-isomer based o starting material is relatively low.

Scott, Crisp and Stille, *J. Amer. Chem. Soc.*, 106, 4630(1984) described the palladium-catalyzed coupling of organotins with electrophiles facilitated by the addition of zinc chloride.

Scott and Stille, *J. Amer. Chem. Soc.*, 108, 3033(1986) described the palladium-catalyzed coupling reaction of several vinyl triflates with organostannanes such as, for example, vinyltributylstannane to yield a product having the vinyl group bonded to the carbon atom which has been vacated by the triflate group.

In view of the desirability to improve the processes to produce 3-vinylcephem derivatives having the preferred cis(Z)-stereoisomeric configuration, it has been conceived to apply a stereospecific synthetic route for constructing the Z-propenyl side chain at C(3) of the cephem nucleus utilizing the palladium-catalyzed coupling of a suitably functionalized cephem with cis(Z)-propenyltributylstannane.

Starting with the readily available 3-hydroxycephems and derivatives thereof, including the trifluoromethylsulfonate (triflate) and methanesulfonate and chloro and diphenylphosphate derivates, coupling with the above-mentioned organometallic agents was explored. It was found that the above coupling reactions were unsatisfactory when carried-out according to conditions reported by Scott and Stille (loc. cit.). The coupling between diphenylmethyl 7-(phenylacetamido)-3-triflyloxy-3-cephem-4-carboxylate and stannanes was unsatisfactory when carried out under literature conditions. The use of Pd((C$_6$H$_5$)$_3$P)$_4$-LiCl in THF led largely to the 3-chloro derivative of the above-mentioned cephem, which readily isomerized to the Δ$^2$-cephem while giving only trace amounts of the desired cephem. Use of ZnCl$_2$ in place of LiCl did not yield any of the Δ$^2$-cephem by-product. However, conversion to the desired product was so slow when carried out in refluxing THF that extensive decomposition of the starting triflate took place. Consequently the desired product, diphenylmethyl 7-(phenyl- acetamido)-3-(Z-1-propenyl)-3-cephem-4-carboxylate, was obtained only in very poor yield.

SUMMARY OF THE INVENTION

It has been discovered that coupling between 3-triflyloxycephems and certain unsaturated hydrocarbylstannanes (unsaturated hydrocarbyltrialkyl stannanes) can be induced to form a carbon-carbon bond at the 3-position of the cephem nucleus in satisfactory yield and, in the case of the 1-alkenyl and 1-polyalkenyl derivatives, with substantially complete stereospecificity (i.e., greater than 99% stereospeciicity). This is accomplished by carrying out the coupling reaction at room temperature in the presence of a relatively polar aprotic solvent, a Pdo or a PdII compound, certain metal halides, and a phosphine.

DETAILED DESCRIPTION OF THE INVENTION

This invention is a process for the production of a -hydrocarbyl-3-cephem derivative represented by the formula

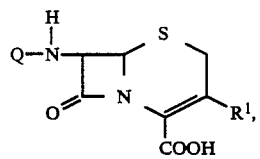

Formula I

R$^1$ represents a hydrocarbyl group selected from unsubstituted and substituted 1-alkenyl, conjugated and unconjugated 1-polyalkenyl, 1-alkynyl, and carbocyclic and heterocyclic aryl and wherein Q represents a group selected from H; an acyl group, R-CO-, wherein R is an organic group having 1-20 carbon atoms and is selected from (a) unsubstituted and substituted carbocyclic and heterocyclic aryl, (b) unsubstituted and substituted, straight-chain and branched-chain, alkyl, (c) unsubstituted and substituted carboxyclic and heterocyclic aralkyl, (d) unsubstituted and substituted carbocyclic and heterocyclic cycloalkyl, (e) unsubstituted and substituted alkenyl, (f) unsubstituted and substituted cycloalkenyl, and (g) unsubstituted and substituted alkynyl; an unsubstituted and substituted trialkylsilyloxycarbonyl and triarylsilyloxycarbonyl; and trialkysilyl and triarylsilyl groups, wherein, when substituted, the alkyl cycloalkyl, alkenyl, cycloalkenyl and alkynyl group may be substituted with 1 to 3 substituents selected from halo, hydroxy, alkoxy, amino, mono- and dialkylamino, nitro, carboxyl, alkoxycarbonyl, oximino, and cyano groups and the aryl group may be substituted with 1 to 3 alkyl, hydroxy, alkoxy, halo, amino, mono- and dialkylamino, nitro, carboxyl, alkoxycarbonyl, and cyano groups and pharmaceutically acceptable acid addition and base salts and esters thereof, comprising the steps of:

(a) providing a 3-trifluoromethanesulfonyloxy-3cephem starting compound in a relatively polar aprotic solvent;

(b) contacting the starting compound from step (a) above with at least an equimolar amount of a hydrocarbyltrialkylstannane in the presence of about 1-10 mole % of a palladium compound and about 3-30 mole % of a phosphine reagent and 0-7 molar equivalents of a metal halide under conditions effective to induce chemical reactivity; and (c) recovering the 3-hydrocarbyl-3-cephem product from the reaction mixture from step (b).

By use of the process according to this invention, we have obtained several novel compounds which we were unsuccessful in obtaining when employing procedures known and reported previously.

In another aspect, this invention is the novel starting 3-trifluoromethanesulfonyloxy-3-cephem having the formula

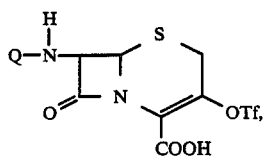

Formula II wherein
Tf represents the trifluoromethanesulfonyloxy, $CF_3SO_2-$, group; and Q represents a group selected from H; an acyl group, R—CO—, wherein R is an organic group having 1–20 carbon atoms and is selected from (a) unsubstituted and substituted, carbocyclic and heterocyclic aryl, (b) unsubstituted and substituted, straight-chain and branched-chain, alkyl, (c) unsubstituted and substituted carbocyclic and heterocyclic aralkyl, (d) unsubstituted and substituted carbocyclic and heterocyclic cycloalkyl, (e) unsubstituted and substituted alkenyl, (f) unsubstituted and substituted cycloalkenyl, and (g) unsubstituted and substituted alkynyl; an unsubstituted and substituted trialkylsilyloxycarbonyl and triarylsilyloxycarbonyl; and trialkylsilyl and triarylsilyl groups, wherein, when substituted, the alkyl, cycloalkyl, alkenyl, cycloalkenyl and alkynyl group may be substituted with 1 to 3 substituents selected from halo, hydroxy, alkoxy, amino, mono- and dialkylamino, nitro, carboxyl, alkoxycarbonyl, oximino, and cyano groups and the aryl group may be substituted with 1 to 3 alkyl, hydroxy, alkoxy, halo, amino, mono- and dialkylamino, nitro, carboxyl, alkoxycarbonyl, and cyano groups and pharmaceutically acceptable acid addition and base salts and esters thereof.

By way of example but without limitation, Q in the above formulas I and II may be unsubstituted and substituted hydrocarbyl such as phenacyl ($\phi CO$); benzoyl ($\phi,CH_2CO$), t-butyloxycarbonyl (t-BuOCO); a group represented by the formula

wherein G is 2- or 3-thienyl or unsubstituted and substituted phenyl and G' is hydroxy, formyloxy, acetoxy, carboxy, sulfo, or amino and substituted amino; a group represented by the formula

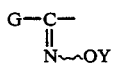

wherein G has the meaning given above and Y is H, methyl or acetyl; a group represented by the formula G—$(Z)_m$—$CH_2$—wherein G has the meaning given above, m is 0 (zero) or 1, and Z is O (Oxygen) or S (sulfur); a group represented by the formula

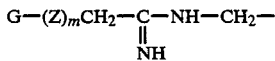

wherein G, Z and m have the meanings given above; and

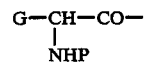

wherein and P is any one of well known protecting groups conventionally used in cephalosporin chemistry with amino, hydroxy and carboxyl groups such as, for example, benzyl, diphenylmethyl, and the like.

The starting 3-trifluoromethanesulfonyloxy-3-cephem (also referred to as 3-triflyloxy-3-cephem wherein the acronym "triflyl" or "triflate" is used to designate the trifluoromethanesulfonyl group) can be readily obtained starting from the known 3-hydroxycephems. The starting 3-triflyloxy-3-cephem may bear various substituents on the 3-cephem nucleus as are known to those skilled in the art to which this invention pertains. The carboxyl group at the 4-position may be in the form of an ester or salt derivative thereof. The 7-position of the 3-cephem nucleus may bear an unsubstituted or substituted amino group wherein the substituent may be selected from any substituent known and reported in the literature. By way of example but without limitation, the 4-carboxyl group may be present as the diphenylmethyl carboxylate ester and the 7-position substituent may be the phenylacetamido or t-butyloxycarbonylamino group.

The aprotic solvent used in the process of this invention should be relatively polar. Thus, the solvent may be selected from 1-methyl-2-pyrrolidinone, tetrahydrofuran (THF), nitriles such as acetonitrile, dimethylsulfoxide (DMSO), dimethylformamide (DMF), ethers such as glyme and dioxane, hexamethylphosphoric amide (HMPA), acetone, nitromethane and nitrobenzene. Preferably, the solvent is selected from 1-methyl-2-pyrrolidinone, THF, acetonitrile, DMSO and DMF. More preferably, the solvent is selected from N-methylpyrrolidinone, THF and acetonitrile. Most preferably, the solvent is 1-methyl-2-pyrrolidinone.

By the expression "hydrocarbyl" with reference to the 3-hydrocarbyl substituent on the cephem nucleus derived from the hydrocarbyltrialkylstannane is meant unsubstituted and substituted alkenyl, unconjugated and conjugated polyalkenyl, alkynyl, and aryltrialkylstannanes, for example, 1-alkenyl- and 1-dienyl, 1-alkynyl- and aryltributylstannanes. Although the 1-alkenyl, 1-dienyl, 1-alkynyl and aryl group may be any such group, preferred are the $C_2$–$C_4$ 1-alkenyl and 1-alkynyl groups including, for example, —C(CH_3)=CH_2, H_2C=CH—, CH_3CH=CH—, (CH )_2C=CH—, CH_3—CHC—, and H_2C=C(OC_2H_5)— bonded to the —Sn(C_4H_9)_3 (or -SnBu_3) group. Representative of the 1-polyalkenyl group are the CH_3—CH=C=CH— and H_2C=CH—CH=CH— groups. With reference to heterocyclic aryl and heterocyclic aralkyl as the "hydrocarbyl" group by the expression "hydrocarbyl" is meant 2-, 3- or 4-pyridyl and -pyridylmethyl, 2-imidazolyl and imidazolylmethyl, and 2-thiazolyl and -thiazolylmethyl, 2- or 3-furyl and -furylmethyl, 2-pyrryl and -pyrrylmethyl, 2-thienyl and -thienyl methyl and salts thereof. More preferably, the process of the invention is useful to produce the 1-alkenyl and 1-alkynyl cephem derivatives. Most preferably, the process of the invention is especially useful to produce the 3-(Z-1-propenyl)-, i.e. 3-(Z-CH=CHCH3)-, 3-cephem, the 3-(propen-2-yl)-3-cephem, and the -3-(1-propynyl)-3-cephem derivatives.

The phosphine reagent may be selected from phosphine compound such as, for example, triphenylphosphine, tri-(3-fluorophenyl)-phosphine, tri-(3-chlorophenyl)phosphine, tri-(3-methoxyphenyl)-phosphine, diphenylmethylphosphine, dimethylphenylphosphine, tributylphosphine, tri-(2-thienyl)-phosphine, and tri-(2-furyl)phosphine. Phosphite compounds such as, for example, trimethyl and triethyl and triphenyl and tri-isopropyl phosphites may be substituted for the above-mentioned phosphine compounds. Also, chelating phosphines such as, for example, bis-diphenylphosphinoethane and bis-diphenylphosphinopropane may be substituted for the above phosphines. Preferably, the phosphine is tri-(2-furyl)-phosphine.

Although any Pd compound may be used in the process of this invention, preferably the Pd compound is selected from a Pd° compound such as bis(dibenzylidene-acetonyl)palladium [Pd(dba)₂] and a Pd$^{II}$ compound such as Pd(OAc)₂, and PdCl₂. The first-named Pd reagent [Pd(dba)₂] is especially advantageous in the process according to this invention.

The metal halide used in combination with the Pd compound in the process according to this invention is selected from $ZnCl_2$, $ZnBr_2$, LiCl, LiBr, LiI, $MgCl_2$, $MgBr_2$, $HgCl_2$ and boron and aluminum and cadmium halides (Cl and Br). Preferably, the metal halide is selected from $ZnCl_2$ and $ZnBr_2$, most preferably, $ZnCl_2$ Representative of the process according to the present invention is the following equation:

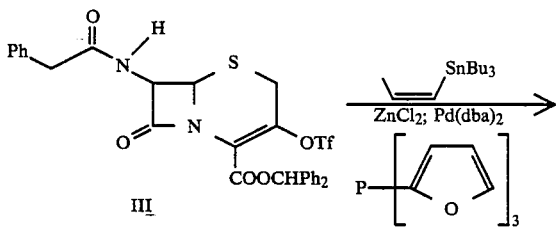

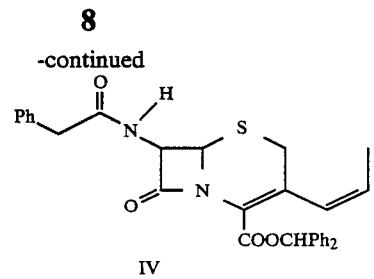

IV

A general experimental procedure for carrying out the process of this invention, with reference to the foregoing equation, follows:

Triflate III (107) mg, 0.169 mmol) in dry 1-methyl-2pyrrolidinone (3 mL) was treated with the appropriate stannane (0.20 mmol, in 1 mL 1-methyl-2-pyrrolidinone). Zinc chloride (52 mg, 0.38 mmol), Pd(dba)2 (2.45 mg, 0.0042 mmol) and tri-(2-furyl)-phosphine (2.0 mg, 0.0085 mmol) were then added. The dark solution was stirred under Argon at 25°-50° C. for about 25 hr. The product was isolated by flash chromatography on Si₂ and characterized by elemental analysis, ¹H-NMR and mass spectroscopy.

The final product may be recovered from the coupling reaction mixture by techniques which are convention in the cephalosporin and penicillin arts, such as by that procedure described above in the general experimental procedure.

The following table illustrates but a few representative hydrocarbyltributylstannanes, resulting products from reaction thereof with the triflate, III, illustrated above, reaction time and yield (%) of product according to the process of this invention.

Example 5 illustrating the preparation of a 3-(desmethyl)-3-cephem is outside the scope of the invention described and claimed herein but is included t illustrate the utility of the process according to the invention.

In view of the results obtained as illustrated in the examples, the time and temperature of the reaction in step (b) of the process according to this invention are not believed to be critical and may range from about 20° C. to about 65° C. for about 1 h to about 75 h, preferably about 25°-50° C. for about 1-72 h, depending on the selection and reactivity of the particular reactants and catalyst system.

TABLE

Palladium-Catalyzed Coupling of III with Stannanes

| Ex. No. | Stannane | Product | Temperature (Time) | % Yield (Isolated) |
| --- | --- | --- | --- | --- |
| 6 | ⟨SnBu₃⟩ | ⟨structure with COOCHPh₃⟩ | 25° C., 1 h | 79 |
| 1 | ⟨SnBu₃⟩(a) | ⟨structure with COOCHPh₃⟩ | 25° C., 16 h | 65 |

TABLE-continued
Palladium-Catalyzed Coupling of III with Stannanes

| Ex. No. | Stannane | Product | Temperature (Time) | % Yield (Isolated) |
|---|---|---|---|---|
| 3 | (CH₃)₂C=CH—SnBu₃ | [cephem product with 3-methylbut-1,3-dienyl substituent; COOCHPh₃] | 25° C., 72 h | 66 |
| 2 | CH₃—C≡C—SnBu₃ | [cephem product with propynyl substituent; COOCHPh₃] | 50° C., 1 h | 50 |
| 4 | MeO—C₆H₄—SnBu₃ | [cephem product with p-methoxyphenyl substituent; COOCHPh₃] | 50° C., 6 h | 57 |
| 7 | CH₂=C(OEt)SnBu₃ | [cephem product with 1-ethoxyvinyl substituent; COOCHPh₃] | 25° C., 16 h | 52 |
| 5 | HSnBu₃[b] | [cephem product, COOCHPh₃] | 65° C., 1 h | 68 |

[a] 98% Z—Stannane gave 97% Z product.
[b] THF was used as a solvent, with 5 equivalents of tin hydride.

The following examples, 1–4 and 6–14, illustrate but a few representative actual procedures for carrying-out the process according to this invention and are not to be construed as limiting the invention in scope. Examples A and B show the preparation of a representative starting material. All parts and percentages are by weight and temperatures are in degrees Celsius unless otherwise indicated.

EXAMPLE A
Diphenylmethyl 7-phenylacetamido-3-hydroxy-3-cephem-4-carboxylate A solution of 3.38 g (0.006 mole) of diphenylmethyl 7-amino-3-hydroxy-3-cephem-4-carboxylate p-toluenesulfonic acid salt[1] and 1.87 g (0.018 mole) of sodium bisulfite in 120 mL of tetrahydrofuran and 30 mL of water was treated dropwise with a solution of 1.41 g (0.009 mole) of phenyl acetyl chloride in 10 mL of tetrahydrofuran. After addition of the acid chloride was complete, the reaction mixture was stirred at room temperature for 2 hrs. The tetrahydrofuran was then removed from the reaction mix at reduced pressure and the aqueous concentrate extracted with ethyl acetate. The organic extract was washed twice with 5% sodium bicarbonate and twice with brine. Finally, the organic solvent was removed at reduced pressure leaving a solid foam residue. The reside was chromatographed on 100 g of silica gel yielding 1.85 g (61.6%) of diphenylmethyl 7-phenylacetamido-3-hydroxy-3-cephem-4-carboxylate. The nuclear magnetic resonance spectrum was consistent for the desired structure.

[1] E Scartazzini, and H. Bickel, Helv. Chim. Acta, 1974, 57, 1919.

EXAMPLE B

Diphenylmethyl 7-phenylacetamido-3-(trifluoromethylsulfonyloxy)-3-cephem-4-carboxylate To 1.57 g (0.00313 mole) of diphenylmethyl 7-phenylacetamido-3-hydroxy-3-cephem-4-carboxylate in 63 mL of methylene chloride was added 0.546 mL (0.00313 mole) of N,N-diisopropylethylamine and the mixture stirred at -20o for 10 min. under a nitrogen atmosphere. Then 0.633 mL (0.00376 mole) of trifluoromethanesulfonic anhydride was added to the mix and stirring at −20° continued for 20 min. The reaction mix was diluted to 400 mL volume by the addition of methylene chloride. To the organic solution was added 100 mL of 0.25 N hydrochloric acid. The phases were separated and the methylene chloride phase was washed successively with water, dilute sodium bicarbonate, 0.25 N hydrochloric acid and water. The organic layer was dried over magnesium sulfate. The sulfate was removed by filtration and the solvent removed at reduced pressure yielding 1.37 g (69.2%) of diphenylmethyl 7-phenylacetamido:-3-(trifluoromethylsulfonyloxy)-3-cephem-4-carboxylate. The nuclear magnetic resonance spectrum was consistent for the desired structure.

Anal. Calcd. for $C_{29}H_{23}N_2O_7S_2F_3$: C, 55.06; H, 3.66; N, 4.43; S, 10.14. Found: C, 55.28; H, 3.66; N, 3.94; S, 10.68.

EXAMPLE 1

Diphenylmethyl 7-phenylacetamido-3-(Z-1-propenyl)-3-cephem-4-carboxylate

A solution of 0.226 g (0.00358 mole) of diphenylmethyl 7-phenylacetamido-3-(trifluoromethylsulfonyloxy)-3-cephem-4-carboxylate, 0.130 g (0.00039 mole) of Z-1-propenyl tri-n-butylstannane, 0.0033 g (0.000014 mole) of tri[2-furyl)phosphine and 0.0041 g (0.000007 mole) of palladium(0) bis(dibenzylidene acetone) in 4 mL of tetrahydrofuran, under an argon atmosphere, was degassed at reduced pressure for 30 seconds. Then a solution of 0.097 g (0.00072 mole) of zinc chloride in 1 mL of tetrahydrofuran was added all at once. The reaction mixture was stirred at room temperature for 16 hrs. The mix was then diluted with ethyl acetate and washed with dilute ammonium chloride solution. The organic solvent was removed at reduced pressure and replaced with acetonitrile. The acetonitrile solution was washed three times with n-pentane and the solvent again removed at reduced pressure. The residue was chromatographed on silica gel to yield 0.123 g (65%) of diphenylmethyl 7-phenylacetamido-3-(Z-1-propenyl)-3-cephem-4-carboxylate. The nuclear magnetic resonance spectrum was consistent for the desired structure.

EXAMPLE 2

Diphenylmethyl 7-phenylacetamido-3-(1-propynyl)-3-cephem-4-carboxylate

A mixture of 1.03 g (0.00162 mole) of diphenylmethyl 7-phenylacetyl-3-(trifluoromethylsulfonyloxy)-3-cephem-4-carboxylate, 0.533 g (0.00162 mole) of (1-propynyl)-tri-n-butylstannane, 0.665 g (0.00488 mole) of zinc chloride, 0.030 g (0.00013 mole) of tri(2-furyl)phosphine and 0.00727 g (0.000032 mole) of palladium(II) acetate in 30 mL of dry N,N-dimethylformamide was heated at 65° C. for 2 hrs and at room temperature for 19 hrs under a nitrogen atmosphere. The reaction mixture was diluted with ethyl acetate and the organic solution washed five times with water. The ethyl acetate was removed at reduced pressure and the residue dissolved in acetonitrile. The organic phase was washed two times with n-pentane and the acetonitrile removed at reduced pressure. The residue was purified by reverse-phase chromatography to yield 0.281 g (30%) of diphenylmethyl -7-phenylacetamido-3-(1-propynyl)-3-cephem-4-carboxylate. The nuclear magnetic spectrum was consistent for the desired structure.

Anal. Calcd. for $C_{31}H_{26}N_2O_4S$: 71.24; H, 5.02; N, 5.36; S, 6.14. Found: C, 71.23; H, 5.02; N, 5.30; S, 6.11.

EXAMPLE 3

Diphenylmethyl 7-phenylacetamido-3-(2-methyl-1-propenyl)-3-cephem-4-carboxylate A mixture of 0.105 g (0.000166 mole) of diphenylmethyl 7-phenylacetamido-3-(trifluoromethylsulfonyloxy)-3-cephem-4-carboxylate, 0.070 g (0.0002 mole) of (2-methyl-1-propenyl)tri-n-butylstannane, 0.052 g (0.00038 mole) of zinc chloride and 0.0039 g (0.000016 mole) of tri(2-furyl)phosphine in 4 mL of dry 1-methyl-2-pyrrolidinone, under an Argon atmosphere, was degassed for 30 seconds. Then 0.0049 g (0.000008 mole) of palladium(0) bis(dibenylidene acetone) was added all at once. The reaction mix was stirred at room temperature for 19 hrs. The reaction mix was then diluted with ethyl acetate and the organic phase washed with dilute ammonium chloride. The ethyl acetate was removed at reduced pressure and replaced with acetonitrile. The organic solution was washed with n-pentane and the acetonitrile removed at reduced pressure. The residue was chromatographed on silica gel yielding 0.0603 g (66%) of diphenylmethyl 7-phenylacetamido-3(2-methyl-1-propenyl)-3-cephem-4-carboxylate. The nuclear magnetic resonance and mass spectra were consistent for the desired structure.

Anal. Calcd. for $C_{32}H_{30}N_2O_4S$: C, 71.35; H, 5.61; N, 5.20; S, 5.95. Found: C, 70.97; H, 5.67; N, 5.07; S, 5.42

EXAMPLE 4

Diphenylmethyl 7-phenylacetamido-3-(p-methoxyphenyl)-3-cephem-4-carboxylate

A mixture of 0.1029 g ((0.000163 mole) of diphenylmethyl 7-phenylacetamido-3-(trifluoromethylsulfonyloxy)-3-cephem- -4-carboxylate, 0.0775 g (0.000195 mole) of (p-methoxyphenyl)tri-n-butylstannane, 0.044 g (0.00032 mole) of zinc chloride and 0.00378 g (0.000016 mole) of tri(2-furyl)-phosphine in 4 mL of dry 1-methyl-2-pyrrolidinone, under an argon atmosphere, was degassed for 30 seconds. Then 0.0047 g (0.000008 mole) of palladium(0) bis(dibenzylidene acetone) was added all at once. The reaction mix was stirred at 50° for 5.5 hrs and room temperature for 16 hrs. The reaction mix was then diluted with ethyl acetate and the organic solution washed with dilute ammonium chloride. The ethyl acetate was removed at reduced pressure and replaced with acetonitrile. The organic phase was washed with n-pentane and the acetonitrile removed at reduced pressure. The residue was chromatographed on silica gel to yield 0.0548 g (57%) of diphenylmethyl 7-phenylacetamido-3-(p-methoxyphenyl)-3cephem-4-carboxylate. The nuclear magnetic resonance spectrum was consistent for the desired structure.

Anal. Calcd, for $C_{35}H_{30}N_2O_5S$: C, 71.16; H, 5.12; N, 4.74 Found: C, 70.95; H, 5/18; N, 470.

EXAMPLE 5

(Comparison)

Diphenylmethyl 7-phenylacetamido-3-(desmethyl)-3-cephem4-carboxylate

To a mixture of 0.100 g (0.000158 mole) of diphenylmethyl 7-phenylacetamido- 3-(trifluoromethylsulfonyloxy)-3-cephem-4-carboxylate, 0.065 g (0.00047 mole) of zinc chloride, 0.00293 g (0.000012 mole) of palladium(II) acetate in 3mL of g (0.00074 mole) of palladium(II) acetate in 3mL of g (0.00074 mole) of tri-n-butyltin hydride portionwise. The reaction mix was stirred at 65° for 2 hrs. The reaction mix was then diluted with methylene chloride and the organic solution washed with n-pentane and the solvent removed at reduced pressure. The residue was chromatographed on silica gel to yield 0.053 g (68.5%) of diphenylmethyl 7-phenylacetamido-3(desmethyl)-3-cephem-4-carboxylate. The reaction mix was stirred at 65o for 2 hrs. The reaction mix was then diluted with methylene chloride and the organic solution washed with n-pentane and the solvent removed at reduced pressure. The residue was chromatographed on silica gel to yield 0.053 g (68.5%) of diphenylmethyl 7-phenylacetamido-3(desmethyl)-3-cephem-4-carboxylate. The nuclear magnetic resonance spectrum was consistent for the desired structure.

Anal. Calcd. for : $C_{28}H_{24}N_2O_4S$: 69.40; H, 4.99; N, 5.78; S, 6.62 Found: C, 68.04; H, 4.96; N, 5.52; S, 6.60

EXAMPLE 6

Diphenylmethyl 7-phenylacetamido-3-ethenyl-3-cephem-4-carboxylate

A mixture of 0.4645 g (0.00073 mole) of diphenylmethyl 7-phenylacetamido-3-trifluoromethylsulfonyloxy-3-cephem4-carboxylate, 0.279 g (0.00088 mole) of ethenyl tri-n-butylstannane, 0.200 g (0.00146 mole) of zinc chloride and 0.0068 g (0.000029 mole) of tri-(2-furyl)phosphine in 6 mL of dry 1-methyl-2-pyrrolidinone, under an Argon atmosphere, was degassed for 30 seconds. Then 0.0084 g (0 000014 mole) of palladium(0) bis(dibenzylidene acetone) was added all at once. The reaction mixture was stirred at room temperature for 1 hr. The reaction mix was then diluted with ethyl acetate and the organic solution washed with dilute ammonium chloride. The ethyl acetate was removed at reduced pressure and replaced with acetonitrile. The organic phase was washed with n-pentane and the acetonitrile removed at reduced pressure. The residue was crystallized from ethanol/methylene chloride yielding 0.320 g (85%) of diphenylmethyl 7-phenylacetamido-3-ethenyl-3-cephem-4-carboxylate. The nuclear magnetic resonance spectrum was consistent for the desired structure.

Anal. Calcd. for $C_{30}H_{26}N_2O_4S$: C, 70.56; H, 5.13; N, 5.49; S, 6.28. Found: C, 70.22; H, 5.13; N, 5.21; S, 6.41.

EXAMPLE 7

Diphenylmethyl 7-phenylacetamido-3-(1-ethoxy-1-ethenyl)-3-cephem-4-carboxylate

A mixture of 0.200 g (0.00031 mole) of diphenylmethyl 7-phenylacetamido-3-trifluoromethylsulfonyloxy)-3-cephem-4-carboxylate, 0.115 g (0.000318 mole) of (1-ethoxyvinyl)tri-n-butylstannane, 0.090 g (0.00066 mole) of zinc chloride and 0.,00293 g (0.000012 mole) of tri(2-furyl)phosphine in 6 mL of dry 1-methyl-2-pyrrolidinone, under an Argon atmosphere, was degassed for 30 seconds. Then 0.0036 g (0.000006 mole) of palladium(0) bis(dibenzylidene acetone) was added all at once. The reaction mix was stirred at room temperature for 19 hrs. The reaction mixture was then diluted with ethyl acetate and the organic solution washed with dilute ammonium chloride. The ethyl acetate was removed at reduced pressure and replaced with acetonitrile. The organic solution was washed with n-pentane and the 1 acetonitrile removed at reduced pressure. The residue was chromatographed on silica gel to yield 0.092 g (52%) of diphenylmethyl 7-[phenylacetamido]-3-(1-ethoxy-1-ethenyl)3-cephem-4-carboxylate. The nuclear magnetic resonance spectrum was consistent for the desired structure.

Anal. Calcd. for $C_{32}H_{30}N_2O_5S$: C, 69.29; H, 5.45; N, 5.05; S, 5.78. Found: C, 69.24; H, 5.54; N, 4.89; S, 5.60.

By following substantially the procedures described above in the description of the invention and in the above actual examples except for substitution of the given triflate (Tf) derivative of 7-[2-(4-hydroxyphenyl)-2-amino- acetamido]- and 7 [(Z)-2-(2-aminothiazol-4-yl)-2-methoxyiminoacetamido]-b 3-hydroxy-3-cephem-4-carboxylic acid and certain esters thereof and of the given hydrocarbyltributylstannane shown in the following Table, additional cephem derivatives were produced according to the process of this invention. The starting triflates (Tf) referred to in the following tables are those compounds designated "V" and "VI (a,b)" below having all acidic sites protected using techniques which are conventional in the art to which this invention relates. Following the coupling reaction to obtain the desired 3-hydrocarbyl substitution on the cephem nucleus, the protecting groups can be removed using conventional techniques. Suitable carbonyl protecting groups include aralkyl groups such as benzyl, methoxybenzyl, and diphenylmethyl (benzhydryl); alkyl such as t-butyl; and haloalkyl such as 2, 2, 2-trichloroethyl and the like. Suitable amine and hydroxy protecting groups include trityl and acyl groups such as chloroacetyl, formyl, t-butoxycarbonyl and carbobenzyloxy etc. It is to be understood that, in the formula shown in the table, "Q" represents the cephem nucleus derived from the triflates "V" and "VI (a,b)" and R1 represents the unsaturated alkyl group from the stannane.

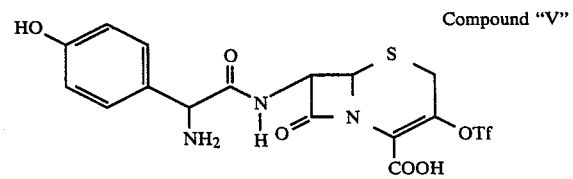

Compound "V"

-continued

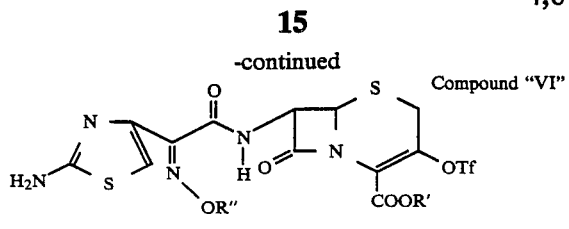

Compound "VI"

VI(a): R' = R'' = H
VI(b): R' = CH₃OCOC(CH₃)₃: R'' = H succinic acid, benzoic acid, tartaric acid, ascorbic acid, methane sulfonic acid, ethanesulfonic acid, p-toluenesulfonic acid, and the like.

Pharmaceutically acceptable base salts are formed by conventional techniques involving reaction of the compounds of Formula I with alkali (Na,K) and alkaline earth (Ba, Zn, Mg) metal bases, more preferably with alkali metal bases such as, for example, dilute solutions of sodium hydroxide, potassium carbonate, and sodium bicarbonate. Also, pharmaceutically acceptable base

TABLE

Additional Examples of Palladium-Catalyzed Coupling of Triflates (Tf) with Stannanes

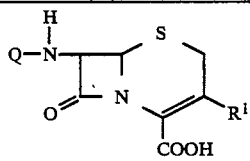

| Ex. No. | Stannane | Tf | Product |
|---|---|---|---|
| 8 | CH₂=CH—SnBu₃ | VI(a) | Q = 7-[2-(2-aminothiazol-4-yl)-2-(Z)—hydroxyiminoacetyl] R¹ = CH=CH₂ mp: 170° C. (dec.) |
| 9 | CH₂=CH—SnBu₃ | VI(a) | Q = 7-[2-(2-aminothiazol-4-yl)-2-(Z)—hydroxyiminoacetyl], pivaloyloxymethyl ester R¹ = CH=CH₂ mp: 130° C. (dec.) |
| 10 | CH₃≡—SnBu₃ | VI(b) | Q = 7-[2-(2-aminothiazol-4-yl)-2-(Z)—hydroxyiminoacetyl] R¹ = C≡C—CH₃ Pivaloyloxymethyl ester mp: 115° C. |
| 11 | (CH₃)₂C=CH—SnBu₃ | VI(a) | Q = 7-[2-(2-aminothiazol-4-yl)-2-(Z)—hydroxyiminoacetyl] R¹ = CH=C(CH₃)₂ mp: <160° C. (grad. dec.) |
| 12 | (CH₃)₂C=CH—SnBu₃ | VI(b) | Q = 7-[2-(2-aminothiazol-4-yl)-2-(Z)—hydroxyiminoacetyl] R¹ = CH=C(CH₃)₂ Pivaloyloxymethyl ester mp: 110°-113° C. |
| 13 | CH₃CH=CH—SnBu₃ | V | Q = 7-[D-2-amino-2-(4-hydroxyphenyl)acetyl] R¹ = CH=CHCH₃ mp: 213-218° C. (dec.) |
| 14 | H₃CH=C=CH—SnBu₃ | V | Q = 7-[D-2-amino-2-(4-hydroxyphenyl)acetyl] R¹ = CH=C=CHCH₃ |

The compounds of Formula I produced according to the process of this invention may be provided as pharmaceutically acceptable acid addition and base salts wherein the anion or cation, respectively, does not contribute significantly to the toxicity of the salt and which salts are compatible with the standard and conventional pharmaceutically acceptable carriers and other conventional adjuvants and excipients customarily employed in producing pharmaceutical compositions adapted for oral or parenteral administration. The acid addition salts are formed by conventional techniques involving reaction for compounds of Formula I with mineral acids such as, for example, hydrochloric acid, hydrobromic acid, phosphoric acid, and sulfuric acid, and with organic carboxylic and sulfonic acids such as, for example, acetic acid, citric acid, maleic acid, salts are formed by conventional techniques involving reaction with amines such as, for example, triethylamine, dibenzylamine, N,N'-dibenzylethylenediamine, procaine and equivalent amines.

Pharmaceutically acceptable esters include those esters which are active per se or which function as pro-drugs by being hydrolyzed in the body to yield the active antibiotic per se. Suitable esters of the latter type include the phenacyl, acetoxymethyl, pivaloyloxymethyl, x-acetoxybenzyl, 3-phthalidyl, 5-indanyl, methoxymethyl, benzoyloxymethy, glycyoxymethyl, and other esters known in the cephalosporin and penicillin arts.

The pharmaceutical compositions of compounds produced according to the process of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing appropriate amounts of the active component, that is, the compound of Formula I according to this invention.

The quantity of active component, that is the compound of Formula I according to this invention, in the pharmaceutical composition and unit dosage form course of treatment depending on the particular situation.

The compounds of formula I produced according to the process of this invention are advantageously administered parenterally, i.e. by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water for injection and a buffer to provide a suitably buffered isotonic solution having a pH of about 3.5-7. Suitable buffering agents include, for example, trisodium orthophosphate, sodium bicarbonate, sodium citrate, N-methylglucamine, L(+)-lysine and L(+)-arginine to name but a few representative buffering agents. The compound according to formula I generally will be dissolved in the carrier in an amount sufficient to provide a pharmaceutically acceptable injectable concentration in the range of about 1 mg/ml to about 400mg/ml of solution. The resulting liquid pharmaceutical composition will be administered so as to obtain the above-mentioned antibacterially effective amount of dosage in the range of from about 100 mg to about 5000 mg per day.

The following table illustrates the activity of several representative compounds produced by the process according to this invention.

TABLE

| | Antibacterial Activity MIC (μg/ml) | | | | | |
|---|---|---|---|---|---|---|
| ORGANISM | Ex. 2 | Ex. 3 | Ex. 1 | Ex. 14 | CEFACLOR | CEPHALEXIN |
| S. pneumoniae | 8 | 0.03 | 0.03 | 2 | 0.13 | 0.5 |
| S. pyogenes | 4 | 0.03 | 0.016 | 2 | 0.13 | 0.25 |
| S. faecalis | 16 | 4 | 8 | >63 | 32 | 63 |
| S. aureus | 4 | 0.06 | 0.13 | 8 | 0.25 | 0.5 |
| S. aureus /50% serum | >16 | 0.06 | 0.5 | 32 | 1 | 1 |
| S. aureus /Pen. Res. | 8 | 0.5 | 1 | 63 | 1 | 8 |
| S. aureus /Meth. Res. | >16 | >125 | >125 | >63 | >125 | >125 |
| E. coli | 16 | 2 | 1 | >63 | 1 | 4 |
| E. coli | 16 | 32 | 4 | >63 | 2 | 4 |
| K. pneumoniae | 16 | 4 | 0.5 | >63 | 0.5 | 4 |
| K. pneumoniae | >16 | >125 | 63 | >63 | 63 | 63 |
| E. cloacae | >16 | 63 | >125 | >63 | >125 | >125 |
| P. mirabilis | 16 | 4 | 1 | 63 | 2 | 4 | thereof may be varied or adjusted widely depending upon the particular application, the potency of the particular compound, and the desired concentration. Generally, the quantity of active component will range between 0.5% to about 90% by weight of the composition.

In therapeutic use for treating, or combatting Gram-positive and Gram-negative bacterial infections in warm-blooded animals, the compounds will be administered at a dosage to obtain and maintain a concentration that is, an amount, or blood-level in the animal undergoing treatment which will be antibacterially effective. Generally, such antibacterially effective amount of dosage will be in the range of from about 100 mg to about 5000 mg per day. It is to be understood that the dosages may vary depending upon the requirement of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the

What is claimed is:

1. A process for the production of a cephem derivative represented by the formula

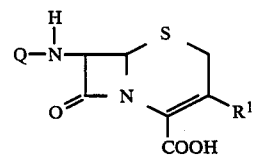

wherein $R^1$ represents a group selected from unsubstituted and substituted 1-alkenyl, conjugated and unconjugated 1-polyalkenyl, 1-alkynyl, aryl or heteroaryl selected from phenyl, 2-, 3-, or 4-pyridyl and -pyridylmethyl, 2-imidazolyl and -imidazolylmethyl, 2-thiazolyl and -thiazolylmethyl, 2-, or 3-furyl and -furylmethyl, 2-pyrryl and -pyrrylmethyl, 2-thienyl and -thienylmethyl; wherein Q represents a group selected form H, t-butyloxycarbonyl, a silyl protecting group, or the acyl group of a known 7-acylamino cephalosporin antibiotic and the aryl, and heteroaryl groups may be substituted with 1 to 3 alkyl, hydroxy, alkoxy, halo, amino, mono- and dialkylamino, nitro, carboxyl, alkoxcarbonyl, and cyano groups and pharmaceutically acceptable acid addition and base salts and esters thereon, comprising the steps of:

(a) providing a 3-trifluoromethanesulfonyloxy-3-cephem starting compound in a relatively polar aprotic solvent;

(b) contacting the starting compound from step (a) above with at least an equimolar amount of $R^1$-tri-alkyl-stannane in the presence of about 1–10 mole % of a pd(0) and Pd(II) compound and about 3–30 mole % of tri-(2-furyl)-phosphine at 25–65? C., protected from atmospheric oxygen, for 1–75 hrs, and (c) recovery of the cephem product from the reaction step (b).

2. A process according to claim 1 wherein the $R^1$-trialkylstannane used in step (b) is selected from the group of $H_2C=CH-SnBu_3$, $CH_3CH=CH-SnBu_3$, $(CH_3)_2C=CH-SnBu_3$, $CH_3-C-C=SnBu_3$, $CH_3O-C_6H_4-SnBu_3$, and $H_2C=C(OC_2H_5)-SnBu_3$.

3. A process according to claim 1 wherein the Pd compound is selected from $Pd(dba)_2$, $Pd(OAc)_2$, and $PdCl_2$.

4. A process according to claim 1 wherein the Pd compound is Pd(dba)2.

5. A process according to claim 2 wherein the Pd compound is Pd(dba)2.

6. The process of claim 1 wherein a metal halide is employed in step (b) in an amount of up to 7 molar equivalents relative to said 3-trifluorolmethanesulfonyloxy- 3-cephem starting compound, and said metal halide is selected from zinc chloride and zinc bromide 7. The process of claim 6 wherein zinc chloride is employed.

* * * * *

UNITED STATES PATENT AND TRADEMARK OFFICE
CERTIFICATE OF CORRECTION

PATENT NO. : 4,870,168
DATED : Sep. 26, 1989
INVENTOR(S) : Stephen R. Baker, Vittorio Farina, Chester Sapino, Jr.

It is certified that error appears in the above-identified patent and that said Letters Patent is hereby corrected as shown below:

Column 1, line 56, delete "-66$^3$" and in its place insert -- - $\Delta^3$ --.

Column 1, line 68, after the word "formula" insert --$R_3P=CR^3R^4$ --.

Column 5, line 40, delete "phenacyl" and insert -- benzoyl --.

Column 5, line 40, delete "benzoyl" and insert -- phenylacetyl --.

Column 6, line 51, delete (CH )2C≡CH-, and insert -- $(CH_3)_2C=CH-$ --.

Column 6, line 52, delete "$CH_3$-CHC-" and insert $CH_3C\equiv$ C- --.

Column 8, line 22, delete "$Si_2$" and insert -- $SiO_2$ --.

Column 8, line 27, delete "convention" and insert -- conventional --.

Column 19, line 13, in Claim 1, delete "pd" and insert -- Pd --.

Column 20, line 2, delete "$CH_3$-C-C$\equiv SNBu_3$" and insert

-- $CH_3C\equiv C-SnBu_3$ --.

Signed and Sealed this

Fourth Day of June, 1991

Attest:

HARRY F. MANBECK, JR.

*Attesting Officer*      *Commissioner of Patents and Trademarks*